United States Patent [19]

Shiokawa et al.

[11] Patent Number: 5,508,413
[45] Date of Patent: Apr. 16, 1996

[54] (+)-5-ISOPROPYL 3-METHYL 2-CYANO-6 METHYL-4-(3-NITROPHENYL)-1,4-DIHYDROPYRIDINE-3,5-DICARBOXYLATE

[75] Inventors: Youichi Shiokawa; Kazuo Okumura, both of Osaka, Japan

[73] Assignee: Fujisawa Pharmaceutical Co., Ltd., Osaka, Japan

[21] Appl. No.: 662,507

[22] Filed: Mar. 22, 1991

Related U.S. Application Data

[63] Continuation of Ser. No. 90,091, Aug. 27, 1987, abandoned.
[51] Int. Cl.$^6$ .................. C07D 213/84; C07D 213/80
[52] U.S. Cl. .................................. 546/286; 546/322
[58] Field of Search .................................. 546/286

[56] References Cited

U.S. PATENT DOCUMENTS

| | | | |
|---|---|---|---|
| 4,284,634 | 8/1981 | Sato | 514/344 |
| 4,338,322 | 7/1982 | Sato | 514/344 |

OTHER PUBLICATIONS

Jacques et al., Enantiomers, Racemates, And Resolutions, pp. 251–263 Wiley–Interscience Publishers (1981).
Jacques et al., Enantiomers, Racemates and Resolutions, pp. 251–263, Wiley–Interscience publishers 1983.

*Primary Examiner*—Alan L. Rotman
*Attorney, Agent, or Firm*—Oblon, Spivak, McClelland, Maier & Neustadt

[57] ABSTRACT

This invention relates to novel (+)-5-isopropyl 3-methyl 2-cyano-6-methyl-4-(3-nitrophenyl)-1,4-dihydropyridine-3,5-dicarboxylate.

More particularly, it relates to novel (+)-5-isopropyl 3-methyl 2-cyano-6-methyl-4-(3-nitrophenyl)-1,4-dihydropyridine-3,5-dicarboxylate, which has pharmacological activities such as hypotensive and vasodilating activities, to a pharmaceutical composition comprising the same and to a method for treating hypertension, cardiovascular diseases, and the like.

Accordingly, one object of this invention is to provide novel (+)-5-isopropyl 3-methyl 2-cyano-6-methyl-4-(3-nitrophenyl)-1,4-dihydropyridine-3,5-dicarboxylate, which is of use for treating hyperxtension, cardiovascular diseases, and the like.

2 Claims, No Drawings

(+)-5-ISOPROPYL 3-METHYL 2-CYANO-6 METHYL-4-(3-NITROPHENYL)-1, 4-DIHYDROPYRIDINE-3, 5-DICARBOXYLATE

This application is a continuation of application Ser. No. 07/090,091, filed on Aug. 27, 1987, now abandoned.

This invention relates to novel (+)-5-isopropyl 3-methyl 2-cyano-6-methyl-4-(3-nitrophenyl)-1,4-dihydropyridine-3,5-dicarboxylate.

More particularly, it relates to novel (+)-5-isopropyl 3-methyl 2-cyano-6-methyl-4-(3-nitrophenyl)-1,4-dihydropyridine- 3,5-dicarboxylate, which has pharmacological activities such as hypotensive and vasodilating activities, to a pharmaceutical composition comprising the same and to a method for treating hypertension, cardiovascular diseases, and the like.

Accordingly, one object of this invention is to provide novel (+)-5-isopropyl 3-methyl 2-cyano-6-methyl-4-(3-nitrophenyl)- 1,4-dihydropyridine-3,5-dicarboxylate, which is of use for treating hypertension, cardiovascular diseases, and the like.

Another object of this invention is to provide a pharmaceutical composition comprising, as an active component, novel (+)-5-isopropyl 3-methyl 2-cyano-6-methyl- 4-(3-nitrophenyl)-1,4-dihydropyridine-3,5-dicarboxylate in association with pharmaceutically acceptable, substantially non-toxic carrier or excipient.

A further object of this invention is to provide a method for treating hypertension and cardiovascular diseases such as coronary insufficiency, angina pectoris and myocardial infarction which comprises administering the same to human or mammals.

With respect to the state of the prior arts in this field, optically inactive, racemic 5-isopropyl 3-methyl 2-cyano-6-methyl-4-(3-nitrophenyl)-1,4-dihydropyridine-3,5-dicarboxylate is known and described, for example, in the U.S. Pat. No. 4,338,322.

This racemic compound possesses strong hypotensive and vasodilating activities and is now eagerly being developed worldwidely by the assignee of this invention as a generic name "Nilvadipine".

Nowever, Nilvadipine is only slightly soluble in water, and therefore, for example, when orally administered, the absorbability of said drug into a body is not so good. Accordingly, hypotensive and vasodilating agents having good solubility in water and much stronger and more lasting effect are highly desired.

Under such situations, as a result of an earnest study, the inventors of this invention have succeeded for the first time in optically resolving the dextrorotatory methyl 5-carboxy-2-cyano-6-methyl-4-(3-nitrophenyl)-1,4-dihydropyridine-3-carboxylate from its racemate and could obtain the dextrorotatory compound of this invention based on said success, which possesses good solubility and more potent pharmacological activities.

The dextrorotatory compound of this invention can be produced from the racemic methyl 5-carboxy-2-cyano-6-methyl- 4-(3-nitrophenyl)-1,4-dihydropyridine-3-carboxylate by the following steps [I] and [II].

Step [I]: Optical Resolution racemic methyl 5-carboxy-2-cyano-6-methyl-
4-(3-nitrophenyl)-1,4-dihydropyridine-3-
carboxylate

| optical resolution
↓

(+)-methyl 5-carboxy-2-cyano-6-methyl-4-
(3-nitrophenyl)-1,4-dihydropyridine-3-
carboxylate Step [II]: Esterification (+)-methyl 5-carboxy-2-cyano-6-methyl-4-(3-nitro-
phenyl)-1,4-dihydropyridine-3-carboxylate

| esterification
↓

(+)-5-isopropyl 3-methyl 2-cyano-6-methyl-4-
(3-nitrophenyl)-1,4-dihydropyridine-3,5-
dicarboxylate Hereinbelow, the Steps [I] and [II] for production of the dextrorotatory compound of this invention are explained in detail.

Step [I]

The optical resolution can be carried out by a conventional method, for example, by (i) transforming the racemic methyl 5-carboxy-2-cyano-6-methyl- 4-(3-nitrophenyl)-1,4-dihydropyridine-3-carboxylate to diastereoisomers with an optically active base such as cinchonine, (ii) precipitating the desired diastereoisomer in the solvent, and then (iii) neutralizing said diastereoisomer with an acid.

However, in order to produce the (+)-methyl 5-carboxy-2-cyano-6-methyl-4-(3-nitrophenyl)-1,4-dihydropyridine-3-carboxylate in good purity and in high yield, it is preferable to take the following optical resolution steps 1 to 4.

racemic methyl 5-carboxy-2-cyano-6-methyl-
4-(3-nitrophenyl)-1,4-dihydropyridine-3-
carboxylate (Compound I)

| Step 1
| cinchonidine
↓ diastereoisomeric salt of (−)-methyl 5-carboxy-
2-cyano-6-methyl-4-(3-nitrophenyl)-1,4-dihydro-
pyridine-3-carboxylate (Compound II) and
diastereoisomeric salt of (+)-methyl 5-carboxy-
2-cyano-6-methyl-4-(3-nitrophenyl)-1,4-dihydro-
pyridine-3-carboxylate (Compound III)

| Step 2
| neutralization by an acid
↓ a mixture of (+)-methyl 5-carboxy-2-cyano-6-
methyl-4-(3-nitrophenyl)-1,4-dihydropyridine-
3-carboxylate (Compound IV) and (−)-methyl
5-carboxy-2-cyano-6-methyl-4-(3-nitrophenyl)-
1,4-dihydropyridine-3-carboxylate (Compound V)

| Step 3
| cinchonine
↓ diastereoisomeric salt of (+)-methyl 5-carboxy-
2-cyano-6-methyl-4-(3-nitrophenyl)-1,4-dihydro-
pyridine-3-carboxylate (Compound VI)

| Step 4
| neutralization by an acid
↓

(+)-methyl 5-carboxy-2-cyano-6-methyl-4-(3-nitro-
phenyl)-1,4-dihydropyridine-3-carboxylate
(Compound IV)

The detailed explanation of these Steps 1 to 4 are as follows.

Step 1

A mixture of diastereoisomeric compounds (II) and (III) can be prepared by reacting the racemic compound (I) with cinchonidine.

This step is carried out in a solvent capable of precipitating the diastereoisomeric compound (II) selectively as much as possible and such a solvent may be methanol, and the like.

The reaction temperature is not restrictive and the reaction is usually carried out under warming to heating.

In this step, some of the diastereoisomeric compound (II) are precipitated due to the difference of the solubility between the compounds (II) and (III) in the solvent, and the resultant precipitates are removed by a conventional method such as filtration, decantation, and the like.

The mother liquor after the removal of the compound (II) contains the compound (III) and the unprecipitated compound (II).

Step 2

A mixture of the dextrorotatory 5-carboxy compound (IV) and the levorotatory 5-carboxy compound (V) can be prepared by neutralizing the mixture of the diastereoisomeric compounds (III) and (II) obtained in the Step 1 by an acid.

This step can be carried out by a conventional method which is applicable to transformation of a salt of a carboxy group to a free carboxy group.

Suitable acid used in this step may include inorganic or organic acid such as hydrochloric acid, sulfuric acid, nitric acid, formic acid, and the like.

Step 3

Diastereoisomeric salt of (+)-methyl 5-carboxy-2-cyano-6-methyl-4-(3-nitrophenyl)-1,4-dihydropyridine-3-carboxylate (VI) can be prepared by reacting a mixture of the compounds (IV) and (V) with cinchonine.

This step can be carried out by substantially the same method as that of the Step 1, and therefore the reaction conditions, etc. can be referred to those of the Step 1.

In this step, it is preferable to use a solvent which is capable of precipitating the diastereoisomeric compound (VI) selectively as much as possible (e.g. ethyl acetate, etc.).

According to this step, though the diastereoisomeric dextrorotatory compound (VI) and the corresponding levorotatory compound are prepared, only the former dextrorotatory compound is precipitated due to the difference of their solubility.

Step 4

The dextrorotatory 5-carboxy compound (IV) can be prepared by neutralizing the diastereoisomeric compound (VI) with an acid.

This step can be carried out by substantially the same method as that of the Step 2, and therefore the examples of the acid can be referred to those of the Step 2.

Step [II]

The (+)-5-isopropyl 3-methyl 2-cyano-6-methyl-4-(3-nitrophenyl)- 1,4-dihydropyridine-3,5-dicarboxylate of this invention can be prepared by esterifying the dextrorotatory 5-carboxy compound (IV).

The esterification of this step can be carried out by a conventional method, for example, by transforming the compound (IV) to the activated form and then reacting it with isopropyl alcohol.

Suitable activated form of the 5-carboxy compound (IV) may include acid halide (e.g. acid chloride, acid bromide, etc.), activated ester formed by ethyl chloroformate, isopropyl chloroformate, etc., and the like.

This reaction can usually be carried out in the presence of a conventional base such as alkali metal carbonate (e.g. sodium carbonate, potassium carbonate, etc,), alkaline earth metal carbonate (e.g. calcium carbonate, magnesium carbonate, etc.), alkali metal bicarbonate (e.g. sodium bicarbonate, potassium bicarbonate, etc.), alkaline earth metal bicarbonate (e.g. calcium bicarbonate, magnesium bicarbonate, etc.), alkali metal hydride (e.g. sodium hydride, potassium hydride, etc.), alkaline earth metal hydride (e.g. calcium hydride, etc.), trialkylamine (e.g. trimethylamine, triethylamine, triisopropylamine, etc.), pyridine compounds (e.g. pyridine, dimethylaminopyridine, picoline, lutidine, etc.), and the like.

In case that the compound (IV) is used in a free carboxy form, the esterification can be carried out in the presence of a conventional condensing agent such as. carbodiimide compounds (e.g. N,N'-dimethylcarbodiimide, N,N'-diethylcarbodiimide, N,N'-diisopropylcarbodiimide, etc.), and the like.

This esterification is usually carried out in a conventional solvent which does not adversely affect the reaction such as methylene chloride, ethylene chloride, and the like.

The reaction temperature is not restrictive and this esterification is usually carried out at ambient temperature to under cooling.

The (+)-5-isopropyl 3-methyl 2-cyano-6-methyl-4-(3-nitrophenyl)- 1,4-dihydropyridine-3,5-dicarboxylate of this invention has higher solubility and much stronger and more lasting hypotensive and vasodilating activities as compared to its optically inactive racemate, i.e., Nilvadipine, and therefore is of use as hypotensive and vasodilating agents for treating hypertension and cardiovascular diseases such as coronary insufficiency, angina pectoris and myocardial infarction.

For the purpose of showing the utility of the dextrorotatory compound of this invention, the pharmacological test and solubility test results are shown hereinbelow.

[A] Measurement of Arterial Blood Pressure in Anesthetized Dogs

Test Method

Mongrel dogs weighing 11.8 to 19.0 kg were used. The dogs were anesthetized by intraperitoneal injection of pentobarbital sodium (35 mg/kg). The blood pressure was measured with a pressure transducer in the left femoral artery. The values of blood pressure were recorded on a polygraph. The right femoral vein was cannulated and the cumulative dose (0.01, 0.032, 0.1, 0.32, 1, 3.2, 10, 32 and 100 µg/kg) of the solution of Test Compounds dissolved in a mixture of polyethylene glycol, ethanol and water was intravenously injected in a volume of 0.2 ml/kg.

Test Compounds (+)-5-isopropyl 3-methyl 2-cyano-6-methyl-4-(3-nitrophenyl)- 1,4-dihydropyridine-3,5-dicarboxylate of this invention (hereinafter referred to as Test Compound A);

(±)-5-isopropyl 3-methyl 2-cyano-6-methyl-4-(3-nitrophenyl)- 1,4-dihydropyridine-3,5-dicarboxylate described in Example 19 of the U.S. Pat. No. 4,338,322 (hereinafter referred to as Nilvadipine);

Test Results

The values of blood pressure were shown in the following table with an expression of mm/Hg.

| Test Compounds | Normal | Cumulative Dose (µg/kg) | | | | | |
|---|---|---|---|---|---|---|---|
| | | 0.32 | 1 | 3.2 | 10 | 32 | 100 |
| A | 120 ± 6 | 117 ± 6 (−2 ± 1) | 114 ± 6 (−5 ± 1) | 101 ± 7 (−16 ± 2) | 74 ± 6 (−39 ± 2) | 64 ± 7 (−47 ± 4) | 58 ± 6 (−52 ± 3) |
| Nilvadipine | 98 ± 6 | 104 ± 6 (+6 ± 1 | 103 ± 5 (+5 ± 1) | 100 ± 4 (−3 ± 2) | 90 ± 3 (−7 ± 5 | 83 ± 5 (−15 ± 6) | 65 ± 6 (−34 ± 6) | note: The values of the parentheses mean the ratio of blood pressure change (%) in each dose as compared to the normal blood pressure.

[B] Solubility Test

Test Method

Solubility of Test Compound A and Nilvadipine in water was measured at ambient temperature.

Test Results

The solubility of each test compounds are shown in the following table.

| Test Compounds | Solubility (µg/ml) |
|---|---|
| A | 4.7 |
| Nilvadipine | 0.6 |

For therapeutical purpose, the (+)-5-isopropyl 3-methyl 2-cyano-6-methyl-4-(3-nitrophenyl)-1,4-dihydropyridine-3,5-dicarboxylate of this invention may be administered in daily dose of 0.05 mg to 100 mg, preferably 1 mg to 25 mg to the interior of the body.

The pharmaceutical composition of this invention comprises, as an active component, (+)-5-isopropyl 3-methyl 2-cyano-6-methyl-4-(3-nitrophenyl)-1,4-dihydropyridine-3,5-dicarboxylate in association with a pharmaceutically acceptable, substantially nontoxic carrier or excipient. An amount of said active component may be about 0.01 mg to about 500 mg, preferably about 0.1 mg to about 250 mg per dosage unit for oral or parenteral use.

One skilled in the art will recognize that the amount of the active component in the dosage unit form may be determined by considering the administration route as well as the size of the host human or mammals. The active component may usually be formulated in a solid or semisolid form such as tablet, granule, powder, capsule, troche, lozenge, suppository, ointment or plaster, or suspension or solution form such as syrup, injection, emulsion, lemonade, etc., and the like.

A pharmaceutical carrier or excipient includes solid or liquid, non-toxic pharmaceutically acceptable substances. Such a solid or liquid carrier or excipient may be lactose, magnesium stearate, terra alba, sucrose, corn starch, talc, stearic acid, gelatin, agar, pectin, gum acacia, peanut oil, olive oil, sesame oil, cacao butter, ethylene glycol or other conventional ones. Similarly, the carrier or excipient may include a time delay material such as glyceryl monostearate, glyceryl distearate, wax, and the like.

For the purpose of illustrating this invention in more detail, the following examples are given.

EXAMPLE 1

A mixture of racemic methyl 5-carboxy-2-cyano-6-methyl- 4-(3-nitrophenyl)-1,4-dihydropyridine-3-carboxylate (16.7 g) and cinchonidine (14.4 g) in methanol (100 ml) was refluxed for 15 minutes and the reaction solution was allowed to stand at ambient temperature. The resulting precipitates were collected by suction, washed with methanol, and air-dried to give cinchonidine salt of (−)-methyl 5-carboxy- 2-cyano-6-methyl-4-(3-nitrophenyl)-1,4-dihydropyridine-3-carboxylate (11.74 g).

The mother liquor was evaporated in vacuo. The crystalline residue was washed with a mixture of ethyl acetate and-diisopropyl ether and extracted with ethyl acetate after an addition of 2N hydrochloric acid (40 ml). The extract was washed with brine, dried over magnesium sulfate, and evaporated in vacuo to give a mixture of (+)- and (−)-methyl 5-carboxy-2-cyano-6-methyl-4-(3-nitrophenyl)- 1,4-dihydropyridine-3-carboxylate (11.15 g).

This mixture (11.15 g) and cinchonine (9.54 g) were dissolved in ethyl acetate under heating and then the solution was allowed to stand at ambient temperature. The resulting precipitates were collected by suction, washed with ethyl acetate., and recrystallized from ethanol to give cinchonine salt of (+)-methyl 5-carboxy-2-cyano-6-methyl- 4-(3-nitrophenyl)-1,4-dihydropyridine-3-carboxylate (7.62 g).

mp: >164° C. (decomp.) $[\alpha]_D^{20}$: +243.2° (c=1.0, $CH_3OH$)

EXAMPLE 2

To a suspension of the cinchonine salt of (+)-methyl 5-carboxy-2-cyano-6-methyl-4-(3-nitrophenyl)-1,4-dihydropyridine- 3-carboxylate (7.41 g) in ethyl acetate (50 ml) was added 2N hydrochloric acid (20 ml) with stirring and then the aqueous layer was removed. The organic layer was washed with brine, dried over magnesium sulfate, and evaporated in vacuo to give (+)-methyl 5-carboxy-2-cyano-6-methyl-4-(3-nitrophenyl)- 1,4-dihydropyridine-3-carboxylate (3.67 g).

mp: 203° C. (decomp.) $[\alpha]_D^{20}$: +234.1° (c=1.0, $CH_3OH$)

NMR(DMSO-$d_6$, δ)): 2.34(3H,s), 3.71(3H,s), 5.13(1H,s), 7.56–7.82(2H,m), 7.91–8.25(2H,m), 10.25 (1H, broad s).

EXAMPLE 3

Phosphorus pentachloride (2.46 g) was added to a suspension of (+)-methyl 5-carboxy-2-cyano-6-methyl-4-( 3-nitrophenyl) -1,4-dihydropyridine-3-carboxylate (3.12 g) in methylene chloride (30 ml) under ice-cooling, and the mixture was stirred for 30 minutes. Then, a solution of isopropyl alcohol (1.4 g) in methylene chloride (10 ml) was added dropwise thereto over a period of 10 minutes. After being stirred for 20 minutes, 5% aqueous sodium carbonate ( 30 ml ) was added to the reaction solution and then stirred at ambient temperature for an hour. The organic layer was separated and the aqueous layer was extracted with methylene chloride. The combined organic layer was washed with brine, dried over magnesium sulfate, and evaporated in vacuo. The residue was purified by column chromatography on silica gel (75 g) using a mixture of benzene and ethyl acetate (10:1) as an eluent. The eluate was evaporated in vacuo and the residue was crystallized from diisopropyl ether to give (+)-5-isopropyl 3-methyl 2-cyano-6-methyl-4-(3-nitrophenyl)-1,4-dihydropyridine-3,5-dicarboxylate (3.34 g).

mp: 120°–122° C.

$[\alpha]_D^{20}$: +222.4° (c=1.0, $CH_3OH$)

NMR ($CDCl_3$, δ) ): 1.09(3H,d,J=6.5Hz), 1.26(3H,d,J= 6.5Hz), 2.40 (3H,s), 3.76 (3H,s), 4.97 (1H,septet,J=6.5Hz), 5.17 (1H, s), 6.96 (1H, broad s), 7.21–7.77 (2H,m), 7.95–8.21 (2H,m).

Elementary Analysis: Calculated for $C_{19}H_{19}N_3O_6$: C 59.22; 4.97; N 10.90; Found: C 59.38; 5.08; N 10.98;

EXAMPLE 4

Cinchonidine salt of (−)-methyl 5-carboxy-2-cyano-6-methyl-4-(3-nitrophenyl)-1,4-dihydropyridine-3-carboxylate (11.74 g) was recrystallized from methanol to give the purified one (9.36 g).

mp: 159°–160° C. $[\alpha]_D^{20}$: −198.9° (c=1.0, $CH_3OH$).

To a suspension of this product (9.05 g) in ethyl acetate (50 ml) was added 2N hydrochloric acid (20 ml) with stirring, and then the aqueous layer was removed. The organic layer was washed with brine, dried over magnesium sulfate, and evaporated in vacuo to give (−)-methyl 5-carboxy-2-cyano-6-methyl-4-(3-nitrophenyl)-1,4-dihydropyridine- 3-carboxylate (5.11 g).

mp: 205° C. (decomp.) $[\alpha]_D^{20}$: −230.7° (c=1.0, $CH_3OH$)

NMR (DMSO-$d_6$, δ): 2.34(3H,s), 3.71(3H,s), 5.13(1H,s), 7.56–7.82 (2H,m), 7.91–8.23 (2H,m), 10.25 (1H, broad s).

EXAMPLE 5

(−)-5-Isopropyl 3-methyl 2-cyano-6-methyl-4-(3-nitrophenyl)- 1,4-dihydropyridine-3,5-dicarboxylate (4.9 g) was obtained by reacting (−)-methyl 5-carboxy-2-cyano-6-methyl- 4-(3-nitrophenyl)-1,4-dihydropyridine-3-carboxylate (4.47 g) with phosphorus pentachloride (3.62 g) and isopropyl alcohol (2.5 g) according to a similar manner to that of Example 3.

mp: 120° to 122° C. $[\alpha]_D^{20}$: −219.6° (c=1.0, $CH_3OH$)

NMR ($CDCl_3$, δ): 1.09(3H,d,J=6.5Hz), 1.25(3H,d,J= 6.5Hz), 2.39(3H,s), 3.78(3H,s), 4.98(1H,septet, J=6.5Hz), 5.19(1H,s), 7.0(1H,broad s), 7.25–7.76 (2H,m), 7.96–8.21 (2H,m)

Elementary Analysis

Calculated for $C_{19}H_{19}N_3O_6$: C 59.22; H 4.97; N 10.90; Found: C 59.17; H 4.92; N 10.91.

What is claimed is:

1. A method for enhancing the solubility of a racemic mixture containing the dextro and levo isomers of 5-isopropyl- 3-methyl-2-cyano-6-methyl-4-(3-nitrophenyl)-1,4-dihydropyridine- 3,5-dicarboxylate which comprises:

(a) subjecting racemic methyl 5-carboxy-2-cyano-6-methyl- 4-(3-nitrophenyl)-1,4-dihydropyridine-3-carboxylate to an optical resolution to give (+)-methyl 5-carboxy-2-cyano-6-methyl- 4-(3-nitrophenyl)-1,4-dihydropyridine-3-carboxylate; and (b) subjecting (+)-methyl 5-carboxy-2-cyano-6-methyl-4-( 3-nitrophenyl)-1,4-dihydropyridine-3-carboxylate or activated form thereof to an esterification reaction to give (+)-5-isopropyl 3-methyl 2-cyano-6-methyl-4-(3-nitrophenyl)-1,4-dihydropyridine- 3,5-dicarboxylate.

2. The method of claim 1, which comprises (a) reacting racemic methyl 5-carboxy-2-cyano-6-methyl-4-( 3-nitrophenyl)-1,4-dihydropyridine-3-carboxylate with cinchonidine to give a diastereoisomeric salt of (−)-methyl 5-carboxy- 2-cyano-6-methyl-4-(3-nitrophenyl)-1,4-dihydropyridine- 3-carboxylate and a diastereoisomeric salt of (+)-methyl 5-carboxy-2-cyano-6-methyl-4-(3-nitrophenyl)-1,4-dihydropyridine- 3-carboxylate, and further removing some of the diastereoisomeric salt of (−)-methyl 5-carboxy-2-cyano-6-methyl- 4-(3-nitrophenyl)-1,4-dihydropyridine-3-carboxylate, which is precipitated during the reaction;

(b) neutralizing the product obtained in the above step (a) by an acid to give a mixture of (−)-methyl 5-carboxy-2-cyano- 6-methyl-4-(3-nitrophenyl)-1,4-dihydropyridine-3-carboxylate and (+)-methyl 5-carboxy-2-cyano-6-methyl-4-(3-nitrophenyl)- 1,4-dihydropyridine-3-carboxylate;

(c) reacting the products obtained in the above step (b) with cinchonine and then removing precipitated diastereoisomeric salt of (−)-methyl 5-carboxy-2-cyano-6-methyl- 4-(3-nitrophenyl)-1,4-dihydropyridine-3-carboxylate to give diastereoisomeric salt of (+)-methyl 5-carboxy-2-cyano-6-methyl- 4-(3-nitrophenyl)-1,4-dihydropyridine-3-carboxylate;

(d) neutralizing the product obtained in the above step (c) by an acid to give (+)-methyl 5-carboxy-2-cyano-6-methyl- 4-(3-nitrophenyl)-1,4-dihydropyridine-3-carboxylate; and (e) reacting the product obtained in the above step (d) or its activated form with isopropyl alcohol to give (+)-5-isopropyl 3-methyl 2-cyano-6-methyl-4-(3-nitrophenyl)-1,4-dihydropyridine- 3,5-dicarboxylate.

* * * * *